（12） United States Patent
Wagner

(10) Patent No.: US 8,206,072 B2
(45) Date of Patent: Jun. 26, 2012

(54) QUICK RELEASE NUT

(75) Inventor: Terry W. Wagner, Mishiwaka, IN (US)

(73) Assignee: Zimmer, Inc., Warsaw, IN (US)

( * ) Notice: Subject to any disclaimer, the term of this patent is extended or adjusted under 35 U.S.C. 154(b) by 296 days.

(21) Appl. No.: 12/577,466

(22) Filed: Oct. 12, 2009

(65) Prior Publication Data
US 2011/0085876 A1 Apr. 14, 2011

(51) Int. Cl.
F16B 37/08 (2006.01)

(52) U.S. Cl. .................................. 411/433; 24/132 AA

(58) Field of Classification Search .................. 411/433, 411/437, 539, 540; 24/132 R, 132 AA, 629, 24/633, 636, 644
See application file for complete search history.

(56) References Cited

U.S. PATENT DOCUMENTS

| 844,469 | A | | 2/1907 | Prouty | |
|---|---|---|---|---|---|
| 915,499 | A | | 3/1909 | Stapley | |
| 1,001,042 | A | | 8/1911 | Kadel | |
| 2,676,509 | A | * | 4/1954 | Graham | ......................... 411/433 |
| 2,736,227 | A | | 2/1956 | Stroble | |
| 3,147,662 | A | * | 9/1964 | Snook | ........................... 411/433 |
| 3,393,598 | A | * | 7/1968 | Bettinger | ...................... 411/433 |
| 4,125,049 | A | | 11/1978 | Price, Jr. | |
| 4,132,146 | A | * | 1/1979 | Uhlig | ............................. 411/433 |
| 4,529,068 | A | * | 7/1985 | Gallo | ........................... 188/71.8 |
| 4,974,888 | A | | 12/1990 | Childers | |
| 5,199,675 | A | * | 4/1993 | DeGuchi | ......................... 248/62 |
| 5,749,691 | A | | 5/1998 | Campbell | |
| 5,755,544 | A | | 5/1998 | Muller et al. | |
| 5,779,418 | A | | 7/1998 | Ying-Che | |
| 5,868,538 | A | | 2/1999 | Rathbun | |
| 5,944,467 | A | | 8/1999 | Yuta | |
| 6,523,799 | B2 | | 2/2003 | Su | |
| 6,599,293 | B2 | | 7/2003 | Tague et al. | |
| 6,799,930 | B1 | | 10/2004 | More et al. | |
| 7,416,375 | B2 | | 8/2008 | Virdee | |
| 7,661,915 | B2 | * | 2/2010 | Whipple | ........................ 411/151 |
| 7,946,021 | B1 | * | 5/2011 | Kochanowicz | ............. 29/525.02 |
| 2005/0192673 | A1 | | 9/2005 | Saltzman et al. | |

* cited by examiner

Primary Examiner — Flemming Saether
(74) Attorney, Agent, or Firm — Faegre Baker Daniels

(57) ABSTRACT

A fastener is provided that may be readily threadingly engaged with and/or disengaged from a threaded shaft without the need to threadingly advance the fastener along substantially the entire length of the threaded shaft. In one exemplary embodiment, a quick release nut is provided that includes an upper body portion and a lower body portion that are rotatably connected to one another. Each of the upper body portion and the lower body portion include central apertures extending therethrough with the walls defining the central apertures of the upper and lower body portions being at least partially threaded.

22 Claims, 5 Drawing Sheets

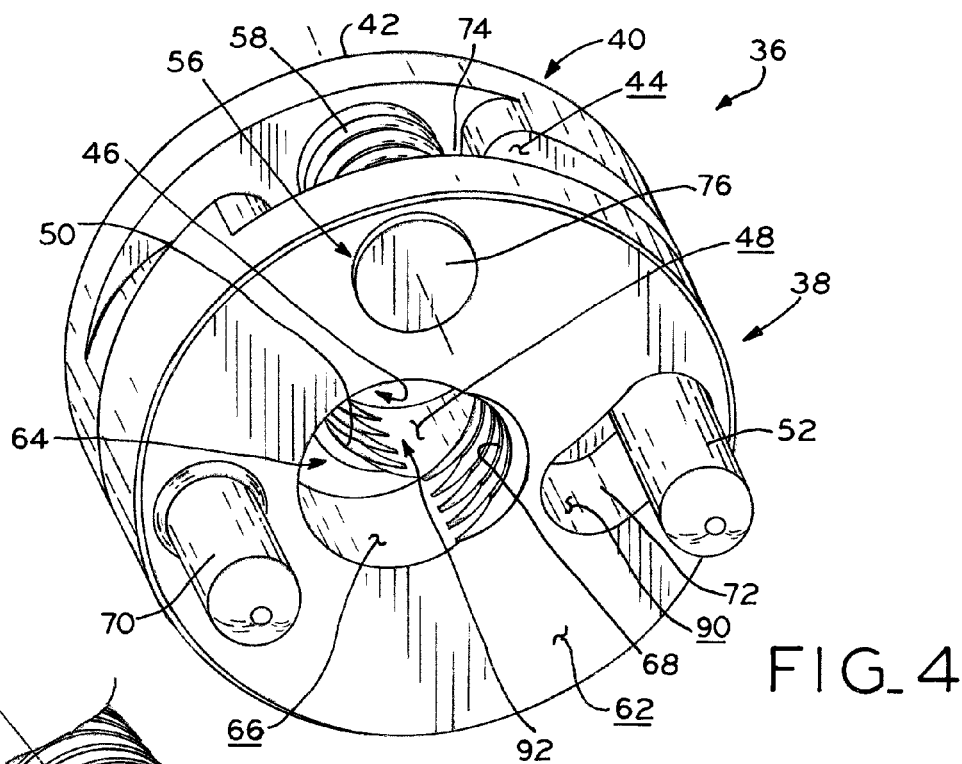
FIG_4
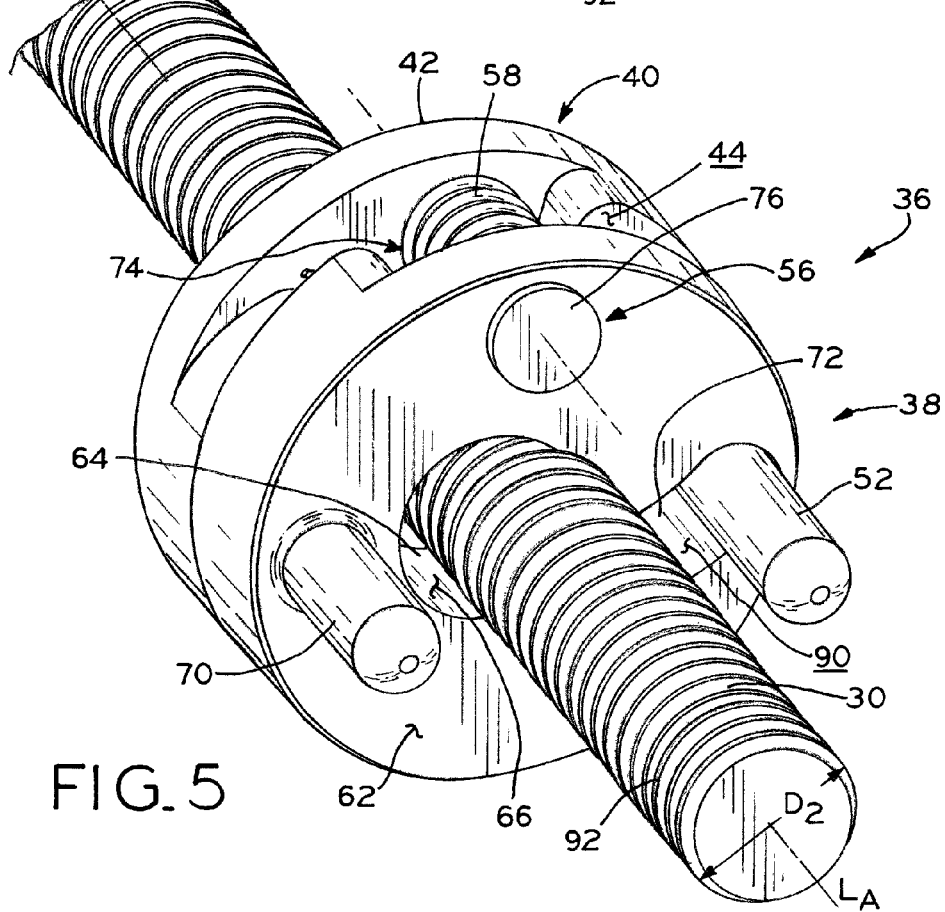
FIG_5

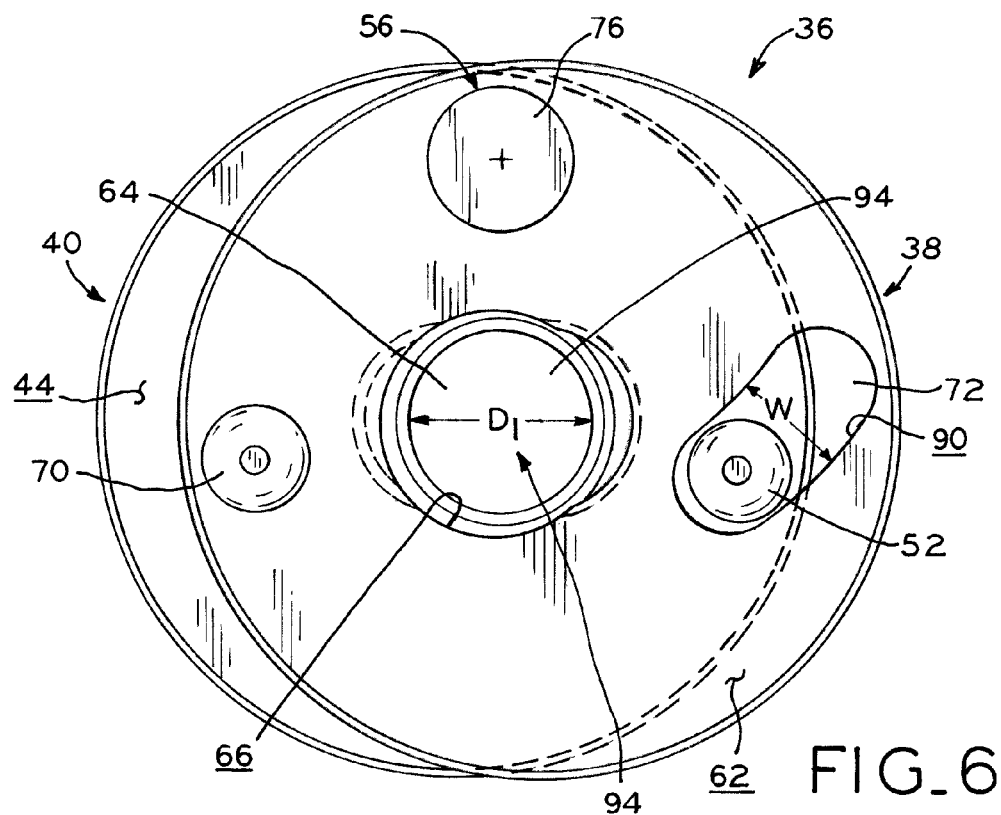
FIG_6
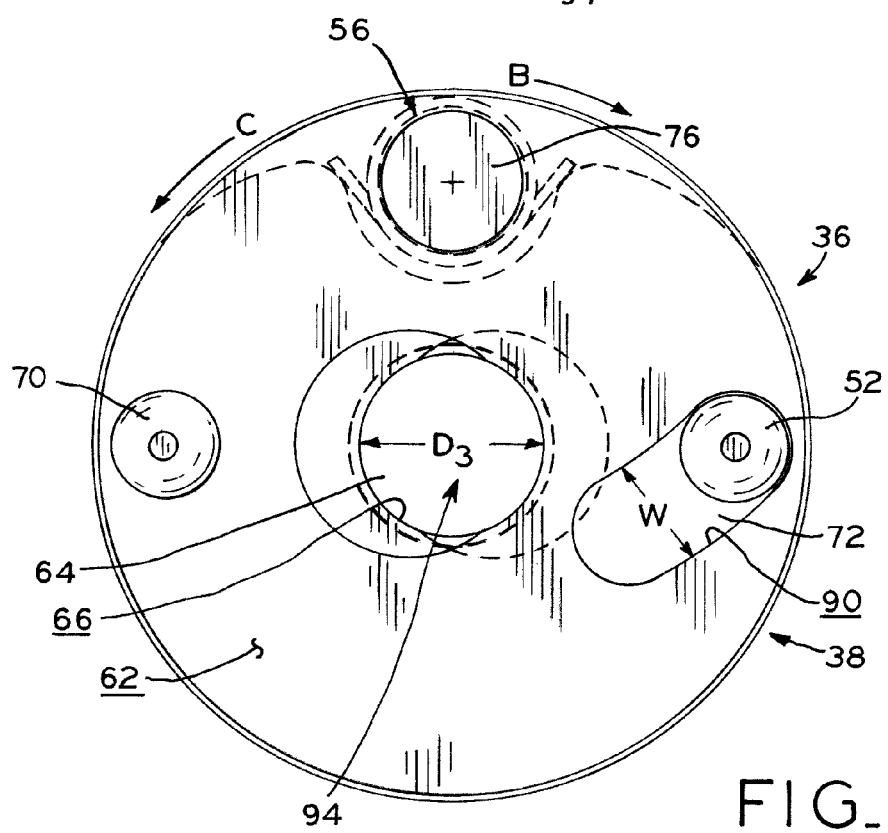
FIG_7

QUICK RELEASE NUT

BACKGROUND

1. Field of the Invention

The present invention relates to fasteners, such as nuts, that may be used in conjunction with a threaded shaft.

2. Description of the Related Art

In order to create a secure connection between opposing components, nuts and bolts may be used. Bolts generally include heads having threaded shafts extending therefrom. The threaded shaft of a bolt is positioned to extend through apertures in opposing first and second components until the head of the bolt is positioned against the first component. A nut having a wall defining a threaded aperture is then threadingly engaged with the threaded shaft of the bolt. The nut is threadingly advanced along the shaft of the bolt by rotating the nut about a longitudinal axis of the shaft until the nut contacts the second component. The nut may then be tightened by additional rotation of the nut about the longitudinal axis of the threaded shaft of the bolt to threadingly advance the nut until the first and second adjacent components are secured together with the desired amount of force. However, when the threaded shaft of the bolt is long, an inordinate amount of time may be required to rotate the nut to threadingly advance the nut along the threaded shaft of the bolt and into contact with the second component.

SUMMARY

The present invention provides a fastener that may be readily threadingly engaged with and/or disengaged from a threaded shaft without the need to threadingly advance the fastener along substantially the entire length of the threaded shaft. In one exemplary embodiment, a quick release nut is provided that includes an upper body portion and a lower body portion that are rotatably connected to one another. Each of the upper body portion and the lower body portion include central apertures extending therethrough with the walls defining the central apertures of the upper and lower body portions being at least partially threaded. By rotating one of the upper and lower body portions in a first direction relative to the other of the upper and lower body portions, the central apertures of the upper and lower body portions may be aligned to create an opening extending through both of the upper and lower body portions, i.e., entirely through the quick release nut, that has a first diameter. The first diameter of the opening extending through the quick release nut is larger than a major diameter of the threads on a threaded shaft with which the quick release nut is to be used. Thus, with the central apertures of the upper and lower body portions in this position, the quick release nut is placed in an open position and the threaded shaft may be received within the opening extending through the quick release nut. The quick release nut may then be advanced along the threaded shaft. Specifically, the quick release nut may be advanced along the threaded shaft solely by translating the quick release nut along the threaded shaft and without the need to rotate the quick release nut about a longitudinal axis of the threaded shaft to threadingly advance the same.

Once the quick release nut has been translated along the threaded shaft and into a desired position, at least one of the opposing upper and lower body portions of the quick release nut may be rotated in an opposite, second direction relative to the other of the upper and lower body portions to cause the central apertures of the upper and lower body portions to be placed in a less aligned or misaligned position that causes the quick release nut to be placed in a closed position. As the central apertures of the upper and lower body portions become less aligned, the amount of overlap between the central apertures of the upper and lower body portions decreases and, correspondingly, the size of the opening extending through the quick release nut, i.e., through both the upper and lower body portions, correspondingly decreases. In a less aligned position, the opening extending through the quick release nut has a second diameter that is less than the major diameter of the threads of the threaded shaft. As a result, once the diameter of the opening extending through the quick release nut decreases to less than the major diameter of the threads of the threaded shaft, the threads defining a portion of the central apertures of the upper and lower body portions of the quick release nut engage the threads on a threaded shaft to threadingly secure the quick release nut to the threaded shaft.

In one exemplary embodiment, the upper and lower body portions of the quick release nut may be biased into the second, less aligned position. For example, the quick release nut may incorporate a spring that operates to bias the upper and lower body portions into the second, less aligned position. As a result, if a surgeon has overcome the biasing force and placed the upper and lower body portions of the quick release nut in a first, more aligned position to advance the quick release nut along a threaded shaft and the surgeon inadvertently releases the quick release nut, the quick release nut will be biased into the second, less aligned position and will lock into threaded engagement with the threaded shaft in the manner described above. Advantageously, this prevents the quick release nut from falling off of a threaded shaft during surgery. A similar advantage is also provided by the use of corresponding apertures that extend through the upper and lower body portions of the quick release nut. Specifically, by forming apertures through the upper and lower body portions of the quick release nut, a threaded shaft is captured within the apertures when the quick release nut is advanced along the threaded shaft. As a result, if a surgeon releases the quick release nut during translation along a threaded shaft, the quick release nut will be prevented from falling off of the threaded shaft by the interaction of the walls defining the apertures in the upper and lower body portions with the threaded shaft.

Once the quick release nut is threadingly engaged with the threaded shaft, additional advancement of the quick release nut along the threaded shaft may be achieved by rotating the quick release nut about a longitudinal axis of the threaded shaft to threadingly advance the quick release nut along the threaded shaft and fully seat the same. For example, threaded advancement of the quick release nut may be desirable to allow an individual to utilize the threaded engagement to easily advance the quick release nut a small distance and to force the adjacent components toward one another. This eliminates the need for an individual to hold or otherwise ensure that the components being secured together are positioned in their final, desired locations before the quick release nut is translated along and initially threadingly engaged with the threaded shaft. Additionally, threaded advancement of the quick release nut may be desirable to allow for the application of a predetermined amount of torque to the quick release nut to ensure a secure connection between components.

In one form thereof, the present invention provides a quick release nut including: a lower body having a lower body top surface, a lower body bottom surface, and a lower body aperture defined by a wall extending between the lower body top surface and the lower body bottom surface, the wall extending 360 degrees about an axis extending through the lower body aperture between the lower body top surface and the lower body bottom surface, at least a portion of the wall defining the lower body aperture having lower body threads; an upper body having an upper body top surface, an upper body bottom surface, and an upper body aperture defined by a wall extending between the upper body top surface and the upper body bottom surface, the wall extending 360 degrees about an axis extending through the upper body aperture between the upper body top surface and the upper body lower surface, at least a portion of the wall defining the upper body aperture having upper body threads, the lower body top surface positioned adjacent the upper body lower surface at least one of the lower body and the upper body moveable relative to the other of the lower body and the upper body; and wherein the lower body aperture and upper body aperture are positionable to cooperatively define a throughbore extending from the upper body top surface to the lower body bottom surface, the lower body aperture and the upper body aperture positionable in a first, more aligned position in which the throughbore has a first diameter and a second, less aligned position in which the throughbore has a second diameter, the first diameter being greater than the second diameter.

In another form thereof, the present invention provides a quick release nut configured for threaded engagement with a connector having a threaded shaft, the threaded shaft of the connector having a major diameter, the nut including: a lower body having a lower body top surface, a lower body bottom surface, and a lower body aperture defined by a wall extending between the lower body top surface and the lower body bottom surface, the wall extending 360 degrees about an axis extending through the lower body aperture between the lower body top surface and the lower body bottom surface, at least a portion of the wall defining the lower body aperture having lower body threads; an upper body having an upper body top surface, an upper body bottom surface, and an upper body aperture defined by a wall extending between the upper body top surface and the upper body bottom surface, the wall extending 360 degrees about an axis extending through the upper body aperture between the upper body top surface and the upper body lower surface, at least a portion of the wall defining the upper body aperture having upper body threads, the lower body top surface positioned adjacent the upper body lower surface, at least one of the lower body and the upper body being moveable relative to the other of the lower body and the upper body; and actuation means for actuating the lower body and the upper body between a first position in which the lower body aperture and upper body aperture cooperate to define a throughbore extending from the upper body top surface to the lower body bottom surface having a first diameter greater than the major diameter of the threaded shaft of the connector and a second position in which the lower body aperture and upper body aperture cooperate to define a throughbore extending from the upper body top surface and the lower body bottom surface having a second diameter no greater than the major diameter of the threaded shaft of the connector.

In yet another form thereof, the present invention provides a quick release nut configured for threaded engagement with a connector having a threaded shaft, the threaded shaft of the connector having a major diameter, the nut including: a lower body having a lower body top surface, a lower body bottom surface, a biasing wall defining an arcuate cutout, and a lower body central aperture defined by a wall extending 360 degrees between the lower body top surface and the lower body bottom surface, the lower body central aperture extending through a mid-portion of the lower body, at least a portion of the wall defining the lower body central aperture having lower body threads, the lower body threads extending no more than 180 degrees around the lower body central aperture; an upper body having an upper body top surface, an upper body bottom surface, a biasing wall defining an arcuate cutout, and an upper body central aperture defined by a wall extending 360 degrees between the upper body top surface and the upper body bottom surface, at least a portion of the wall defining the upper body central aperture having upper body threads, the upper body threads extending no more than 180 degrees around the upper body central aperture; a connecting bar extending between the upper body and the lower body, the connecting bar securing the upper body and the lower body to one another, the connecting bar being rotatably connected to at least one of the upper body and the lower body, wherein the lower body top surface is positioned directly adjacent the upper body lower surface; a torsion spring extending around and positioned on the connecting bar, the torsion spring having a first end and a second end, the first end of the torsion spring contacting the biasing wall of the upper body and the second end of the torsion spring contacting the biasing wall of the lower body, wherein the first end and the second end of the torsion spring exert a biasing force on the lower body and the upper body to rotate the lower body and the upper body from a first position in which the lower body aperture and upper body aperture cooperate to define a throughbore extending from the upper body top surface to the lower body bottom surface having a first diameter greater than the major diameter of the threaded shaft of the connector and a second position in which the lower body aperture and upper body aperture cooperate to define a throughbore extending from the upper body top surface and the lower body bottom surface having a second diameter no greater than the major diameter of the threaded shaft of the connector; and wherein the lower body and the upper body rotate relative to one another about an axis of rotation, the axis of rotation being eccentric to a throughbore axis extending through the center of the throughbore.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 4 is another perspective view of the quick release nut of FIG. 2;

FIG. 5 is a perspective view of the nut of FIG. 4 depicting the quick release nut positioned on a threaded shaft;

FIG. 6 is a plan view of the quick release nut of FIG. 2 depicting the central apertures of the upper and lower body portions of the quick release nut in an open or aligned position; and FIG. 7 is a plan view of the quick release nut of FIG. 2 depicting the central apertures of the upper and lower body portions of the quick release nut in a closed or misaligned position.

Corresponding reference characters indicate corresponding parts throughout the several views. The exemplification set out herein illustrates an exemplary embodiment of the invention, in one form, and such exemplification is not to be construed as limiting the scope of the invention in any manner.

DETAILED DESCRIPTION

Figure 1:
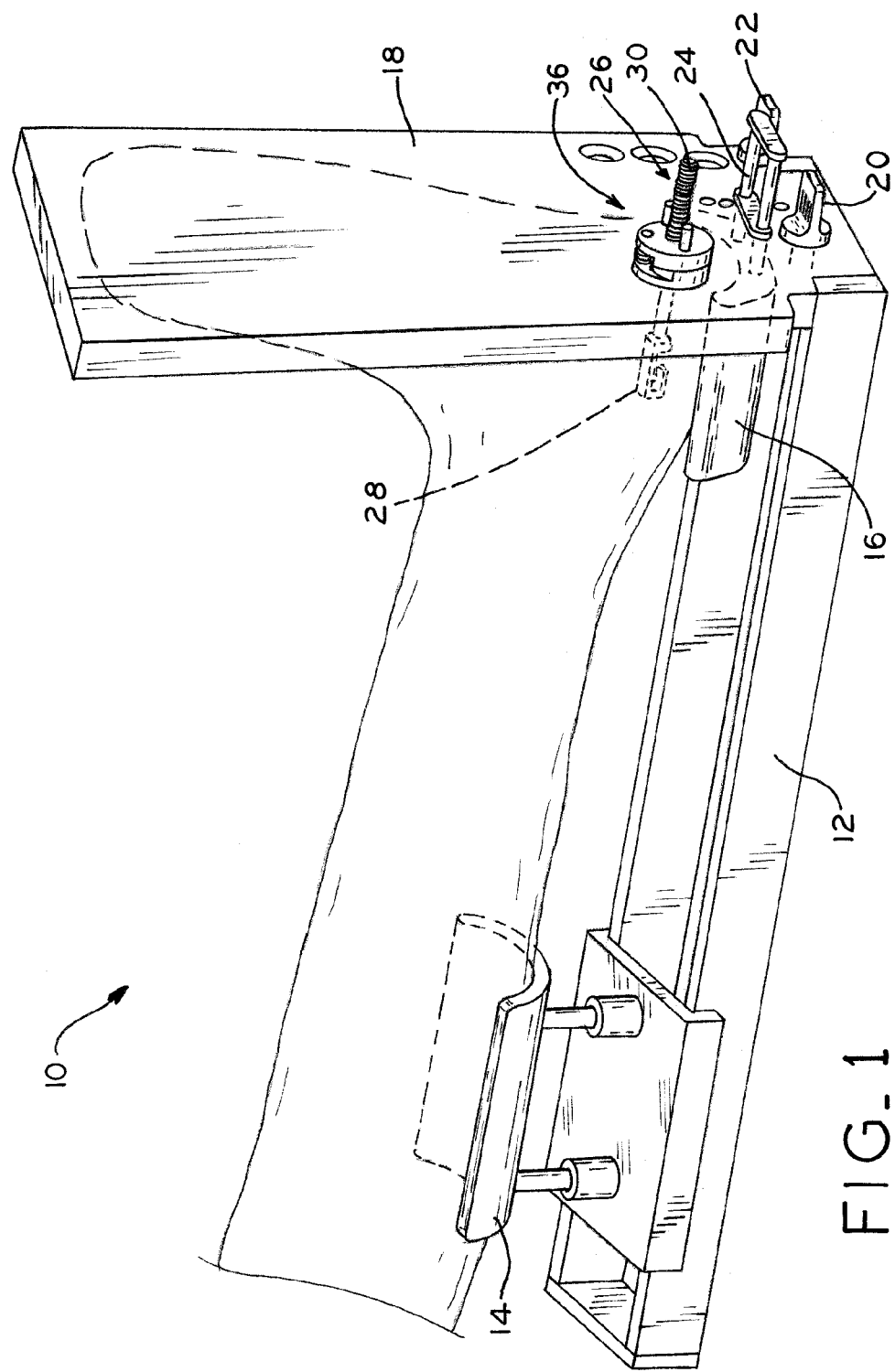
FIG. 1 is a perspective view of the quick release nut of the present invention in use with a support structure to secure a patient's foot in position.
Figure 2:
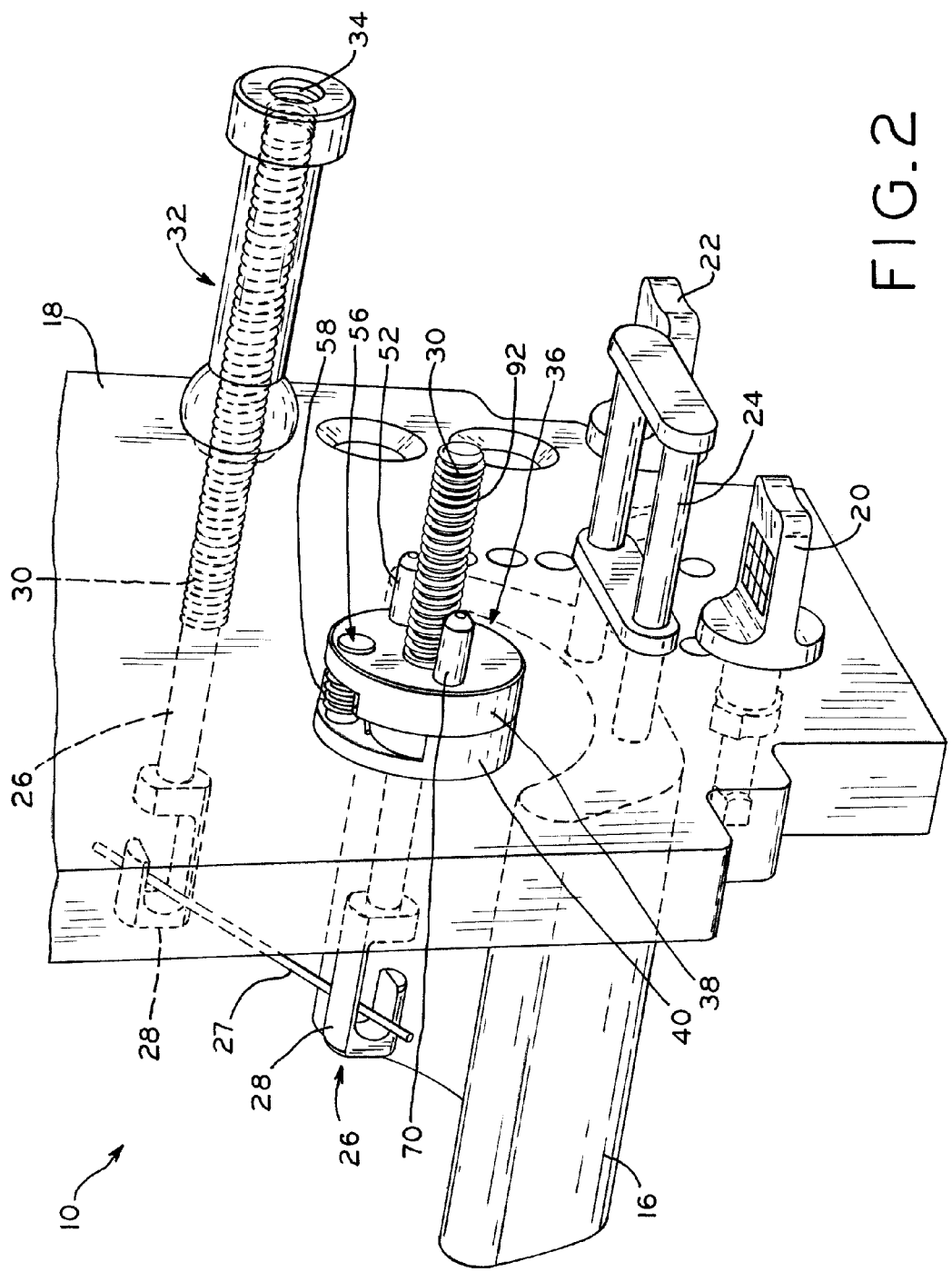
FIG. 2 is an enlarged, partial fragmentary view of the device of FIG. 1 depicting the quick release nut of the present invention and further depicting another connector.

Referring to FIGS. 1 and 2, support structure 10 is shown for supporting a patient's heel and securing the patient's foot in a desired position for surgery. Specifically, support structure 10 includes frame 12, calf support 14, heel support 16, and foot plate 18. Foot plate 18 has a plurality of openings extending therethrough that are configured for the receipt of various connectors or fasteners. For example, connectors 20, 22 are used to secure footplate 18 to frame 12 and connector 24 is used to secure footplate 18 to heel support 16.

With a patient's foot positioned on support structure 10 as shown in FIG. 1, hooked connectors 26 and calcaneous pin 27 (FIG. 2) are used to connect the patient's foot to foot plate 18 and to secure the patient's foot in a desired position. Specifically, calcaneous pin 27 extends through the calcaneous bone (not shown) of the patient's foot and is positioned such that opposing ends of calcaneous pin 27 are positioned on opposing sides of and exterior of the patient's foot. As shown in FIGS. 1 and 2, hooked connectors 26 include hooked heads 28 and threaded shafts 30 extending therefrom. Referring to FIG. 2, hooked heads 28 receive and capture the opposing ends of calcaneous pin 27 that are positioned on the exterior of the patient's foot. Hooked connectors 26 are then connected to foot plate 18 to secure the patient's foot in position. As shown in FIG. 2, hook connectors 26 may be connected to foot plate 18 by using rod 32. Rod 32 includes threaded aperture 34 extending along its entire length. In order to secure hook connector 26 to foot plate 18, rod 32 must be threaded from the end of threaded shaft 30 of hook connector 26 furthest from foot plate 18 until rod 32 contacts foot plate 18, which may require an inordinate amount of time during a surgical procedure.

Figure 3:
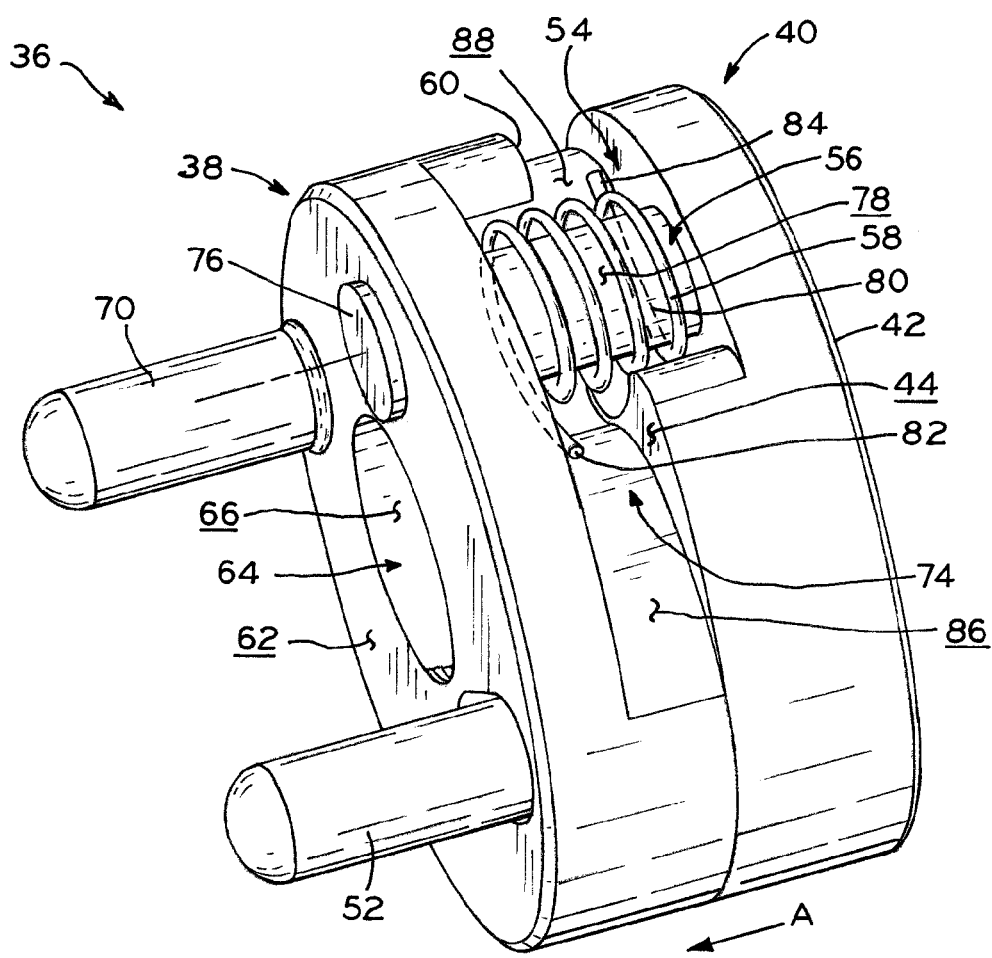
FIG. 3 is a perspective view of the quick release nut of FIG. 2.

In order to eliminate the need to thread rod 32 from the end of threaded shaft 30 furthest from foot plate 18 until rod 32 contacts foot plate 18, quick release nut 36 of the present invention may be used. As shown in FIGS. 1 and 2, quick release nut 36 is utilized to secure hooked connector 26 to foot plate 18 and to correspondingly secure a patient's foot in position. Referring to FIGS. 3 and 4, quick release nut 36 includes upper body portion 38 and lower body portion 40. In one exemplary embodiment, upper and lower body portions 38, 40 are substantially disk-shaped. In another exemplary embodiment, upper and lower body portions 38, 40 are polygonal-shaped so as to allow ease of mating with a tightening tool, such as a wrench or other surgical tool.

Referring to FIGS. 4 and 5, lower body portion 40 includes bottom surface 42 and opposing top surface 44. As shown in FIG. 4, lower body portion 40 includes aperture 46 extending between top surface 44 and bottom surface 42 thereof and defined by wall 48. In one exemplary embodiment, aperture 46 of lower body portion 40 extends through the midportion of lower body portion 40, i.e., extends through the approximate middle of lower body portion 40. Wall 48 defining aperture 46 extends between top surface 44 and bottom surface 42 and includes threads 50. In one exemplary embodiment, wall 48 extends 360° about an axis extending through aperture 46 between top surface 44 and bottom surface 42. In one exemplary embodiment, threads 50 extend no more than 180° along wall 48. In another exemplary embodiment, threads 50 extend for substantially 180° along wall 48. In another exemplary embodiment, threads 50 extend for more than 180° along wall 48. In one exemplary embodiment, wall 48 has a radius that is greater than the radius of threaded shaft 30. In this embodiment, wall 48 may be threaded for more than 180°. However, when quick release nut 36 is in the closed or less aligned position, as described in detail below, threads 50 will contact threaded shaft 30 along no more than 180°. This allows for lower body portion 40 and, correspondingly, threads 50 to be readily rotated and/or translated into and out of threaded engagement with threaded shaft 30, as described in detail below.

Additionally, lower body post 52 extends upwardly from top surface 44 of lower body portion 40. Lower body post 52 may be secured to lower body portion 40 in any known manner, such as by welding. Referring to FIG. 3, lower body portion 40 also includes arcuate cutout 54 configured for receipt of connecting bar 56 and spring 58, as described in detail below.

Referring again to FIGS. 3 and 4, upper body portion 38 includes bottom surface 60, top surface 62, and aperture 64 extending between top surface 62 and bottom surface 60 and defined by wall 66. In one exemplary embodiment, aperture 64 of upper body portion 38 extends through the midportion of upper body portion 38, i.e., extends through the approximate middle of upper body portion 38. Referring to FIG. 3, wall 66 defining aperture 64 extends between top surface 62 and bottom surface 60 and includes threads 68. In one exemplary embodiment, wall 66 extends 360° about an axis extending through aperture 64 between top surface 62 and bottom surface 60. In one exemplary embodiment, threads 68 extend no more than 180° along wall 66. In another exemplary embodiment, threads 68 extend for substantially 180° along wall 66. In another exemplary embodiment, threads 68 extend for more than 180° along wall 66. In one exemplary embodiment, wall 66 has a radius that is greater than the radius of threaded shaft 30. In this embodiment, wall 66 may be threaded for more than 180°. However, when quick release nut 36 is in the closed or less aligned position, as described in detail below, threads 68 will contact threaded shaft 30 along no more than 180°. This allows for upper body portion 38 and, correspondingly, threads 68 to be readily rotated and/or translated into and out of threaded engagement with threaded shaft 30, as described in detail below.

Additionally, in the embodiment in which the radii of wall 48 of lower body portion 40 and wall 66 of upper body portion 38 are greater than the radius of threaded shaft 30, quick release nut 32 may be used with threaded shafts having a radius greater than the radius of threaded shaft 30 and threads 50, 68 may contact the threaded shaft along a greater extent, but still less than 180°. Additionally, quick release nut 32 may be used with threaded shafts having a radius less than the radius of threaded shaft 30 and threads 50, 68 will contact the threaded shaft along a lesser extent than they would contact threaded shaft 30 when used therewith.

Upper body portion 38 also includes upper body post 70 extending from top surface 62 thereof. Upper body post 70 may be secured to upper body portion 38 in any known manner, such as by welding. Additionally, upper body portion 38 includes arcuate lower body post receiving aperture 72. Aperture 72 has a width W (FIG. 6) sized for receipt of lower body post 52 that extends upwardly from lower body portion 40, as described above. Upper body portion 38 also includes arcuate cutout 74 (FIG. 3) that is substantially similar to arcuate cutout 54 of lower body portion 40 and is designed for receipt of connecting bar 56 and spring 58, as described in detail below.

Referring to FIG. 3, connecting bar 56 extends between upper and lower body portions 38, 40 and secures upper and lower body portions 38, 40 to one another. In one exemplary embodiment, connecting bar 56 is fixedly secured to lower body portion 40, such as by welding. In this embodiment, connecting bar 56 is rotatably secured to upper body portion 38 and defines an axis of rotation for upper body portion 38 along the longitudinal axis of connecting bar 56. The axis of rotation defined by connecting bar 56 is eccentric relative to a throughbore axis that extends through the center of apertures 64, 46 of upper and lower body portions 38, 40 when apertures 64, 46 are substantially aligned with one another, as described in detail below.

Connecting bar 56 may be received through a connecting bar receiving aperture (not shown) in upper body portion 38 until head 76 of connecting bar 56 contacts top surface 62 of upper body portion 38. Referring to FIG. 3, head 76 of connecting bar 56 is sized to extend outwardly beyond outer surface 78 of shaft 80 of connecting bar 56, such that, when connecting bar 56 is passed through the connecting bar receiving aperture in upper body portion 38 and secured to lower body portion 40, head 76 prevents translation of upper body portion 38 in a direction away from lower body portion 40 along the longitudinal axis of shaft 80 of connecting bar 56, i.e., in the direction of arrow A of FIG. 3. While upper body portion 38 is described and depicted herein as being rotatable about connecting bar 56, in other exemplary embodiments, lower body portion 40 may be rotatable about connecting bar 56 or, alternatively, both upper and lower body portions 38, 40 may be rotatable about connecting bar 56.

Referring to FIG. 3, spring 58 extends around and is positioned on connecting bar 56. Spring 58 functions to maintain quick release nut 36 in a closed positioned, as described in detail below. In one exemplary embodiment, spring 58 is a torsion spring. As shown in FIG. 3, spring 58 includes opposing ends 82, 84 that contact walls 86, 88 defining arcuate cutouts 74, 54 of upper and lower body portions 38, 40, respectively. Due to the contact between opposing ends 82, 84 of spring 58 and walls 86, 88, respectively, spring 58 exerts a biasing force on upper and lower body portions 38, 40, in the direction of arrows B, C, respectively, of FIG. 7. The biasing force applied by spring 58 to upper and lower body portions 38, 40 functions to bias upper and lower body portions 38, 40 into a closed position, as shown in FIGS. 3 and 4. In this way, spring 58, connecting bar 56 and wall 86, 88 function as an actuation means to actuate the quick release nut of the present disclosure from an open position (described further below) to a closed position. As indicated above, with quick release nut 36 in a closed position, apertures 64, 46 of upper and lower body portions 38, 40 are less aligned or misaligned with one another. With quick release nut 36 in the closed position, which is described in detail below, additional rotation of upper and lower body portions 38, 40 relative to one another as a result of the biasing force applied to upper and lower body portions 38, 40 by spring 58 is prevented by the interaction of lower body post 52 with wall 90 defining lower body post receiving aperture 72 of upper body portion 38. In addition to spring 58 and connecting bar 56, other biasing and/or actuation mechanisms known to those of ordinary skill in the art may be used in conjunction with quick release nut 36, such as a ratchet and pawl or a worm gear.

To position quick release nut 36 on a threaded shaft, as shown in FIG. 5 and described in detail below, quick release nut 36 must be placed in the open position, i.e., in a position in which apertures 64, 46 of upper and lower body portions 38, 40 are substantially aligned. In order to place quick release nut 36 in the open position, i.e., a position in which apertures 64, 46 of upper and lower body portions 38, 40 are more aligned with one another as shown in FIG. 6, the biasing force of spring 58 must be overcome and upper body portion 38 rotated relative to lower body portion 40 about connecting bar 56. Specifically, an individual user may position posts 52, 70 adjacent to their thumb and index finger, respectively, and apply a force to posts 52, 70 in the directions opposite of arrows B, C of FIG. 7 that is sufficient to overcome the biasing force of spring 58. By applying a force to posts 52, 70 that is sufficient to overcome the biasing force of spring 58, upper and lower body portions 38, 40 rotate relative to one another in the directions opposite of arrows B, C, respectively, of FIG. 7. Rotation of upper and lower body portions 38, 40 relative to one another may continue until lower body post 52 extending from lower body portion 40 and into post receiving aperture 72 of upper body portion 38 contacts wall 90 defining post receiving aperture 72. The contact of lower body post 52 with wall 90 provides the individual user with tactile feedback indicating that quick release nut 36 is in the open position. Additionally, the contact between lower body post 52 and wall 90 prevents additional rotation of upper and lower body portions 38, 40 in the directions opposite of arrows B, C. As a result, upper and lower body portions 38, 40 are prevented from over-rotating, i.e., rotating to a position in which apertures 64, 46 of upper and lower body portions 38, 40 start to become less aligned or misaligned.

With quick release nut 36 in the open position, the aligned or more aligned portions of apertures 64, 46 cooperate to define an opening extending through quick release nut 36 that has a diameter $D_1$ (FIG. 6), which is greater than the major diameter of threads of a corresponding threaded shaft, such as threads 92 of threaded shaft 30 of hook connector 26 of FIG. 5, which have a major diameter $D_2$ as shown in FIG. 5. As used herein, the phrase "major diameter" when used with reference to an external thread, such as the thread of a bolt, refers to the diameter extending from a crest to an opposing crest of the thread. With upper and lower body portions 38, 40 rotated to place apertures 64, 46 in an aligned or more aligned position and, correspondingly, to place quick release nut 36 in an open position, quick release nut 36 may be positioned such that threaded shaft 30 extends into opening 94 defined by the cooperation of walls 66, 48 of apertures 64, 46. Quick release nut 36 may then be translated along longitudinal axis LA (FIG. 5) of threaded shaft 30 to advance quick release nut 36 in the direction of foot plate 18, for example, without the need to rotate quick release nut 36 about longitudinal axis LA of threaded shaft 30. Advantageously, by utilizing apertures 64, 46, a threaded shaft may be positioned within and captured by walls 66, 48 defining apertures 64, 46, such that translation of the threaded shaft in a radially outward direction from a centerpoint of apertures 64, 46 is restricted. As a result, once a threaded shaft is positioned within apertures 64, 46, quick release nut 36 is contained on the threaded shaft by walls 66, 48 defining apertures 64, 46.

Once quick release nut 36 has been translated along threaded shaft 30 and into a desired position, the user may release posts 72, 50 and allow the biasing force of spring 58 to rotate upper and lower body portions 38, 40 in directions of arrows B, C (FIG. 5), placing quick release nut 36 into the closed position in which apertures 64, 46 of upper and lower body portions 38, 40 are misaligned with one another, as shown in FIG. 6. As upper and lower body portions 38, 40 are rotated in the direction of arrows B, C by the biasing force exerted on upper and lower body portions 38, 40 by spring 58, as described in detail above, the diameter of opening 94 extending through quick release nut 36 decreases. As the diameter of opening 94 decreases to less than major diameter $D_2$ of threaded shaft 30, threads 68, 50 of walls 66, 48 of apertures 64, 46 threadingly engage threads 92 of threaded shaft 30. Specifically, referring to FIG. 7, with apertures 64, 46 in a misaligned position, such that quick release nut 36 is in a closed position, opening 94 defined by walls 66, 48 of apertures 64, 46 has a diameter $D_3$ that is less than major diameter $D_2$ of threads 92 of threaded shaft 30 (FIG. 5). Once apertures 64, 46 are in the misaligned position and quick release nut 36 is, correspondingly, in the closed position, additional rotation of upper and lower body portions 38, 40 in the directions of arrows B, C is prevented by the interaction of wall 90 of post receiving aperture 72 with lower body post 52.

Further, as shown in FIG. 4, with quick release nut 36 in the closed position, threads 68, 50 of walls 66, 48 that define portions of apertures 64, 46 are aligned with one another to form a substantially continuous thread extending substantially 360° around opening 94 that extends through quick release nut 36 and is cooperatively defined by apertures 64, 46, as shown in FIG. 6. Advantageously, this allows for approximately 360° of threaded engagement between quick release nut 36 and threaded shaft 30. Specifically, approximately 180° of threaded engagement is provided by threads 68 of wall 66 of upper body portion 38 and approximately 180° of threaded engagement is provided by threads 50 of wall 48 of lower body portion 40.

Once quick release nut 36 has been translated along threaded shaft 30 and placed in the closed position to threadingly engage threaded shaft 30, quick release nut 36 may be further advanced along longitudinal axis LA of threaded shaft 30 by rotating quick release nut 36 about longitudinal axis LA of threaded shaft 30. Specifically, in order to advance quick release nut 36 in the direction of foot plate 18 (FIG. 1) and to tighten quick release nut 36 against foot plate 18, quick release nut 36 may be rotated by grasping posts 70, 52 and rotating upper and lower body portions 38, 40 of quick release nut 10 in the direction of arrow C of FIG. 7, respectively. Advantageously, by threading quick release nut 36 along threaded shaft 30 as indicated, quick release nut 36 may be advanced along threaded shaft 30 even after it has been placed in the closed position and threadingly engaged with the threaded shaft, without the need to disengage threads 64, 46 of upper and lower body portions 38, 40 from threaded shaft 30. In one exemplary embodiment, the exterior surfaces of upper and lower body portions 38, 40 are knurled to increase frictional engagement between upper and lower body portions 38, 40 and a user's hand to allow the user to easily grasp and rotate quick release nut 36 in the direction of arrow C without the need to engage posts 70, 52. Additionally, the entire operation of quick release nut 36, as described in detail above, may be performed using only one hand and without the need for any tools. As a result, when quick release nut 36 is used in a surgical setting, a surgeon may use the other hand to perform additional aspects of the surgical procedure while still advancing and/or otherwise manipulating quick release nut 36.

While upper and lower body portions 38, 40 of quick release nut 36 are described and depicted herein as being rotatable relative to one another, upper and lower body portions 38, 40 may instead be configured to translate relative to one another. In this configuration (not shown), one of upper and lower body portions 38, 40 may be translated away from the other of upper and lower body portion 38, 40 to position apertures 64, 46 in a first, aligned or more aligned position and may be translated toward the other of upper and lower body portion 38, 40 to position apertures 64, 46 in a second, less aligned or misaligned position in a similar manner as described in detail above. In this embodiment, upper and lower body portions 38, 40 may be biased into the second, less aligned position by a biasing mechanism in a similar manner as described in detail above with respect to connecting bar 56.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:
1. A quick release nut comprising:
a lower body having a lower body top surface, a lower body bottom surface, and a lower body aperture defined by a wall extending between said lower body top surface and said lower body bottom surface, said wall extending 360 degrees about an axis extending through said lower body aperture between said lower body top surface and said lower body bottom surface, at least a portion of said wall defining said lower body aperture having lower body threads;
an upper body having an upper body top surface, an upper body bottom surface, and an upper body aperture defined by a wall extending between said upper body top surface and said upper body bottom surface, said wall extending 360 degrees about an axis extending through said upper body aperture between said upper body top surface and said upper body bottom surface, at least a portion of said wall defining said upper body aperture having upper body threads, said lower body top surface positioned adjacent said upper body bottom surface, at least one of said lower body and said upper body moveable relative to the other of said lower body and said upper body; and
wherein said lower body aperture and said upper body aperture are positionable to cooperatively define a throughbore extending from said upper body top surface to said lower body bottom surface, said lower body aperture and said upper body aperture positionable in a first, substantially aligned position in which said throughbore has a first diameter and a second, substantially misaligned position in which said throughbore has a second diameter, said first diameter being greater than said second diameter, wherein said upper body is rotatably connected to said lower body, said lower body and said upper body rotatable relative to one another about an axis of rotation, said axis of rotation being eccentric to a throughbore axis extending through a center of said throughbore.

2. The quick release nut of claim 1, further comprising a connecting bar extending between said upper body and said lower body, said connecting bar having a longitudinal axis, at least one of said upper body and said lower body being rotatable about said connecting bar, wherein said longitudinal axis of said connecting bar defines said axis of rotation.

3. The quick release nut of claim 1, further comprising a biasing mechanism for biasing said lower body and said upper body into said second position.

4. The quick release nut of claim 3, wherein said biasing mechanism comprises a torsion spring.

5. The quick release nut of claim 1, wherein said lower body further comprises a lower body post extending from said lower body top surface and said upper body further comprises a post aperture extending from said upper body top surface to said upper body bottom surface, said post aperture receiving said lower body post therein, wherein interaction of said lower body post with a wall defining said post aperture limits movement of said lower body and said upper body relative to one another.

6. The quick release nut of claim 5, wherein said upper body further comprises an upper body post extending from said upper body top surface.

7. A quick release nut comprising:
a lower body having a lower body top surface, a lower body bottom surface, and a lower body aperture defined by a wall extending between said lower body top surface and said lower body bottom surface, said wall extending 360 degrees about an axis extending through said lower body aperture between said lower body top surface and said lower body bottom surface, at least a portion of said wall defining said lower body aperture having lower body threads;
an upper body having an upper body top surface, an upper body bottom surface, and an upper body aperture defined by a wall extending between said upper body top surface and said upper body bottom surface, said wall extending 360 degrees about an axis extending through said upper body aperture between said upper body top surface and said upper body bottom surface, at least a portion of said wall defining said upper body aperture having upper body threads, said lower body top surface positioned adjacent said upper body bottom surface, at least one of said lower body and said upper body moveable relative to the other of said lower body and said upper body; and
wherein said lower body aperture and said upper body aperture are positionable to cooperatively define a throughbore extending from said upper body top surface to said lower body bottom surface, said lower body aperture and said upper body aperture positionable in a first, substantially aligned position in which said throughbore has a first diameter and a second, substantially misaligned position in which said throughbore has a second diameter, said first diameter being greater than said second diameter, wherein said lower body further comprises a lower body post extending from said lower body top surface and said upper body further comprises a post aperture extending from said upper body top surface to said upper body bottom surface, said post aperture receiving said lower body post therein, wherein interaction of said lower body post with a wall defining said post aperture limits movement of said lower body and said upper body relative to one another.

8. The quick release nut of claim 6, wherein said upper body further comprises an upper body post extending from said upper body top surface.

9. A quick release nut configured for threaded engagement with a connector having a threaded shaft, the threaded shaft of the connector having a major diameter, the nut comprising:
a lower body having a lower body top surface, a lower body bottom surface, and a lower body aperture defined by a wall extending between said lower body top surface and said lower body bottom surface, said wall extending 360 degrees about an axis extending through said lower body aperture between said lower body top surface and said lower body bottom surface, at least a portion of said wall defining said lower body aperture having lower body threads;
an upper body having an upper body top surface, an upper body bottom surface, and an upper body aperture defined by a wall extending between said upper body top surface and said upper body bottom surface, said wall extending 360 degrees about an axis extending through said upper body aperture between said upper body top surface and said upper body bottom surface, at least a portion of said wall defining said upper body aperture having upper body threads, said lower body top surface positioned adjacent said upper body bottom surface, at least one of said lower body and said upper body being moveable relative to the other of said lower body and said upper body; and
actuation means for actuating said lower body and said upper body between a first position in which said lower body aperture and said upper body aperture cooperate to define a throughbore extending from said upper body top surface to said lower body bottom surface having a first diameter greater than the major diameter of the threaded shaft of the connector and a second position in which said lower body aperture and said upper body aperture cooperate to define a throughbore extending from said upper body top surface to said lower body bottom surface having a second diameter no greater than the major diameter of the threaded shaft of the connector, wherein said actuation means comprises a connecting bar extending between said upper body and said lower body, said connecting bar having a longitudinal axis, at least one of said upper body and said lower body being rotatable about an axis of rotation defined by said longitudinal axis of said connecting bar.

10. The quick release nut of claim 9, wherein said actuation means further comprises a torsion spring.

11. The quick release nut of claim 9, wherein said connecting bar is rotatably connected to one of said upper body and said lower body and is fixedly connected to the other one of said upper body and said lower body.

12. The quick release nut of claim 9, wherein said connecting bar further comprises a head having a shaft extending outwardly therefrom, said shaft secured to said lower body and said head positioned adjacent to said upper body top surface.

13. The quick release nut of claim 9, wherein said actuation means further comprises a torsion spring extending around and positioned on said connecting bar, said torsion spring having a first end and a second end, said first end of said torsion spring contacting a biasing wall of said upper body, said biasing wall defining an arcuate cutout in said upper body, and said second end of said torsion spring contacting a biasing wall of said lower body, said biasing wall of said lower body defining an arcuate cutout in said lower body.

14. The quick release nut of claim 9, wherein said axis of rotation defined by said connecting bar is eccentric to a throughbore axis extending through the center of said throughbore defined by said lower body aperture and said upper body aperture in said second position.

15. The quick release nut of claim 9, wherein said lower body threads extend no more than 180 degrees around said lower body aperture and said upper body threads extend no more than 180 degrees around said upper body aperture.

16. The quick release nut of claim 9, wherein said lower body further comprises a lower body post extending from said lower body top surface and said upper body further comprises a post aperture extending from said upper body top surface to said upper body bottom surface, said post aperture receiving said lower body post therein, wherein interaction of said lower body post with a wall defining said post aperture limits actuation of said lower body and said upper body relative to one another.

17. The quick release nut of claim 16, wherein said upper body further comprises an upper body post extending from said upper body top surface.

18. A quick release nut configured for threaded engagement with a connector having a threaded shaft, the threaded shaft of the connector having a major diameter, the nut comprising:
- a lower body having a lower body top surface, a lower body bottom surface, and a lower body aperture defined by a wall extending between said lower body top surface and said lower body bottom surface, said wall extending 360 degrees about an axis extending through said lower body aperture between said lower body top surface and said lower body bottom surface, at least a portion of said wall defining said lower body aperture having lower body threads;
- an upper body having an upper body top surface, an upper body bottom surface, and an upper body aperture defined by a wall extending between said upper body top surface and said upper body bottom surface, said wall extending 360 degrees about an axis extending through said upper body aperture between said upper body top surface and said upper body bottom surface, at least a portion of said wall defining said upper body aperture having upper body threads, said lower body top surface positioned adjacent said upper body bottom surface, at least one of said lower body and said upper body being moveable relative to the other of said lower body and said upper body; and
- actuation means for actuating said lower body and said upper body between a first position in which said lower body aperture and said upper body aperture cooperate to define a throughbore extending from said upper body top surface to said lower body bottom surface having a first diameter greater than the major diameter of the threaded shaft of the connector and a second position in which said lower body aperture and said upper body aperture cooperate to define a throughbore extending from said upper body top surface to said lower body bottom surface having a second diameter no greater than the major diameter of the threaded shaft of the connector, wherein said lower body further comprises a lower body post extending from said lower body top surface and said upper body further comprises a post aperture extending from said upper body top surface to said upper body bottom surface, said post aperture receiving said lower body post therein, wherein interaction of said lower body post with a wall defining said post aperture limits actuation of said lower body and said upper body relative to one another.

19. The quick release nut of claim 18, wherein said upper body further comprises an upper body post extending from said upper body top surface.

20. A quick release nut configured for threaded engagement with a connector having a threaded shaft, the threaded shaft of the connector having a major diameter, the nut comprising:
- a lower body having a lower body top surface, a lower body bottom surface, a biasing wall defining an arcuate cutout, and a lower body central aperture defined by a wall extending 360 degrees between said lower body top surface and said lower body bottom surface, said lower body central aperture extending through a mid-portion of said lower body, at least a portion of said wall defining said lower body central aperture having lower body threads, said lower body threads extending no more than 180 degrees around said lower body central aperture;
- an upper body having an upper body top surface, an upper body bottom surface, a biasing wall defining an arcuate cutout, and an upper body central aperture defined by a wall extending 360 degrees between said upper body top surface and said upper body bottom surface, at least a portion of said wall defining said upper body central aperture having upper body threads, said upper body threads extending no more than 180 degrees around said upper body central aperture;
- a connecting bar extending between said upper body and said lower body, said connecting bar securing said upper body and said lower body to one another, said connecting bar being rotatably connected to at least one of said upper body and said lower body, wherein said lower body top surface is positioned directly adjacent said upper body bottom surface;
- a torsion spring extending around and positioned on said connecting bar, said torsion spring having a first end and a second end, said first end of said torsion spring contacting said biasing wall of said upper body and said second end of said torsion spring contacting said biasing wall of said lower body, wherein said first end and said second end of said torsion spring exert a biasing force on said lower body and said upper body to rotate said lower body and said upper body from a first position in which said lower body aperture and said upper body aperture cooperate to define a throughbore extending from said upper body top surface to said lower body bottom surface having a first diameter greater than the major diameter of the threaded shaft of the connector and a second position in which said lower body aperture and said upper body aperture cooperate to define a throughbore extending from said upper body top surface to said lower body bottom surface having a second diameter no greater than the major diameter of the threaded shaft of the connector; and
- wherein said lower body and said upper body rotate relative to one another about an axis of rotation, said axis of rotation being eccentric to a throughbore axis extending through the center of said throughbore defined by said upper body aperture and said lower body aperture in said second position.

21. The quick release nut of claim 20, wherein said lower body further comprises a lower body post extending from said lower body top surface and said upper body further comprises a post aperture extending from said upper body top surface to said upper body bottom surface, said post aperture receiving said lower body post therein, wherein interaction of said lower body post with a wall defining said post aperture limits rotation of said lower body and said upper body relative to one another.

22. The quick release nut of claim 21, wherein said upper body further comprises an upper body post extending from said upper body top surface.

* * * * *

UNITED STATES PATENT AND TRADEMARK OFFICE
CERTIFICATE OF CORRECTION

| | | |
|---|---|---|
| PATENT NO. | : 8,206,072 B2 | Page 1 of 1 |
| APPLICATION NO. | : 12/577466 | |
| DATED | : June 26, 2012 | |
| INVENTOR(S) | : Terry W. Wagner | |

It is certified that error appears in the above-identified patent and that said Letters Patent is hereby corrected as shown below:

In column 11, line 48, in Claim 8, delete "claim 6" and insert --claim 7--, therefor Signed and Sealed this
Thirteenth Day of November, 2012

David J. Kappos
*Director of the United States Patent and Trademark Office*